(12) United States Patent
Trebosc et al.

(10) Patent No.: US 11,207,305 B2
(45) Date of Patent: Dec. 28, 2021

(54) ANTIBIOTIC COMBINATION THERAPIES

(71) Applicant: BIOVERSYS AG, Basel (CH)

(72) Inventors: Vincent Trebosc, Rixheim (FR); Christian Kemmer, Riehen (CH); Glenn E. Dale, Basel (CH); Sergio Lociuro, Basel (CH); Marc Gitzinger, Laufenburg (CH)

(73) Assignee: BIOVERSYS AG, Basel (CH)

( * ) Notice: Subject to any disclaimer, the term of this patent is extended or adjusted under 35 U.S.C. 154(b) by 0 days.

(21) Appl. No.: 16/983,718

(22) Filed: Aug. 3, 2020

(65) Prior Publication Data

US 2021/0077472 A1 Mar. 18, 2021

Related U.S. Application Data

(60) Provisional application No. 62/977,659, filed on Feb. 17, 2020, provisional application No. 62/941,160, filed on Nov. 27, 2019, provisional application No. 62/902,019, filed on Sep. 18, 2019, provisional application No. 62/899,257, filed on Sep. 12, 2019.

(51) Int. Cl.

| A61K 31/438 | (2006.01) |
|---|---|
| A61P 31/04 | (2006.01) |
| A61K 9/00 | (2006.01) |
| A61K 31/546 | (2006.01) |
| A61K 38/12 | (2006.01) |

(52) U.S. Cl.
CPC ......... *A61K 31/438* (2013.01); *A61K 9/0019* (2013.01); *A61K 9/0043* (2013.01); *A61K 9/0053* (2013.01); *A61K 9/0073* (2013.01); *A61K 31/546* (2013.01); *A61K 38/12* (2013.01); *A61P 31/04* (2018.01)

(58) Field of Classification Search
CPC .................................................... A61K 31/438
See application file for complete search history.

(56) References Cited

U.S. PATENT DOCUMENTS

2016/0281143 A1* 9/2016 Holmes .................... C12Q 1/04

OTHER PUBLICATIONS

Gauthier (Clin Infect Dis. Aug. 2013;57(3):359-61), (Year: 2013).*
Falagas et al (Journal of Antimicrobial Chemotherapy, vol. 72, Issue 6, Jun. 2017, pp. 1704-170) (Year: 2017).*
Kunin (Clinical Infectious Diseases, vol. 22, Issue Supplement_1, Apr. 1996, pp. S3-S14).. (Year: 1996).*

* cited by examiner

*Primary Examiner* — Benjamin J Packard
(74) *Attorney, Agent, or Firm* — Brown Rudnick LLP; Thomas C. Meyers

(57) ABSTRACT

The invention provides antibiotic combination therapies for treating an *A. baumannii* infection in a subject. The combination therapies include rifabutin and a second antibiotic, such as colistin and cefiderocol.

20 Claims, 2 Drawing Sheets

ANTIBIOTIC COMBINATION THERAPIES

RELATED APPLICATIONS

This Application claims the benefit of and priority to U.S. Provisional Patent Application Ser. Nos. 62/902,019, filed Sep. 18, 2019, 62/899,257, filed Sep. 12, 2019, 62/941,160, filed Nov. 27, 2019, and 62/977,659, filed Feb. 17, 2020, the content of each of which is incorporated herein in its entirety.

FIELD OF THE INVENTION

The invention relates generally to rifabutin combination therapies for treating *A. baumannii* infections.

BACKGROUND

The emergence of multi-drug resistant (MDR) or extensively-drug resistant (XDR) strains of bacteria over the last few decades has made bacterial infections an increasingly serious public health concern. One bacterial species that poses a major health threat is *Acinetobacter baumannii*, which can cause pneumonia, meningitis, and infections of the blood, urinary tract, and skin. Because *A. baumannii* cells can survive on artificial surfaces for extended periods, the bacterium is readily transmissible in a hospital environment, and most *A. baumannii* infections are nosocomially acquired. For example, many soldiers in the Middle East have been infected with *A. baumannii* while being treated for injuries sustained during combat, and multidrug-resistant strains of the bacterium represent a significant complication in rehabilitation of injured soldiers.

Treatment of *A. baumannii* infections is challenging. Through the use of transposable genetic elements, strains of *A. baumannii* have developed resistance to antibiotics in several different classes, including aminoglycosides, aminocyclitols, tetracyclines, chloramphenicol, and carbapenems. Polymyxins, such as colistin, are typically used as a last resort due to their serious side effects, but some *A. baumannii* strains are resistant to colistin as well (Zubair et al, 2015). Consequently, current tools for treating and preventing illness caused by this bacterium are inadequate for many patients. Significant efforts have been made to find out a solution in order to treat theses nosocomial pathogen, one of which is combined therapy (Levin et al, 1999; Wood et al, 2003). The combinations of two antibiotics have shown different effects on each other and in many cases the effect is synergistic or strengthening but, in some cases, antagonism is observed (Montero et al, 2004; Tripodi et al, 2007). Rifampicin (an antibiotic belonging to the rifamycin class antibiotic like rifabutin) targets the bacterial DNA-dependent RNA polymerase B subunit (rpoB) and is an antibiotic which is frequently used with other antibiotics. Rifampicin (also known as rifampin) has shown synergy with colistin towards *A. baumannii*, however, the result of this combination is dependent on the rifampin's MICs (Giannouli et al, 2012). In particular no synergistic effect of rifampicin and colistin was observed in *A. baumannii* isolates in which elevated rifampicin MICs were due to mutations in the rpoB target gene.

SUMMARY

The invention provides combination therapies that include rifabutin and a second antibiotic, such as a polymyxins (e.g. colistin, polymyxin B, polymyxin B nonapeptide; polymyxin analogues as exemplified by MRX-8,) other cationic antimicrobial peptides (e.g. SPR741; chimeric peptidomimetic antibiotics exemplified by POL7306; octapeptin cyclic peptides) or cefiderocol, for treating *A. baumannii* infections. The invention is based on the finding that rifabutin acts synergistically with certain other antibiotics to inhibit growth of *A. baumannii* cells. The combinations of antibiotics display synergy to a wide range of *A. baumannii* strains. The synergy greatly increases the susceptibility of *A. baumannii* cells to rifabutin and colistin, with some strains displaying over a 500-fold increase in sensitivity to one of those antibiotics used in combination with the other compared to when that antibiotic is used by itself. Moreover, and unexpectedly, combinations of rifabutin and colistin act synergistically to inhibit growth of strains that are resistant to both of those antibiotics when they are provided individually and therefore making those strains susceptible to the combination treatment even when the elevated MICs to rifabutin and rifampicin are due to mutations in the rpoB gene. This observation is in stark contrast to that observed with the combination of rifampicin and colistin where the strains with mutations remain resistant to the combination. Thus, the invention unlocks the therapeutic potential of antibiotics in settings in which they are otherwise impotent and provides effective therapies for treatment of serious *A. baumannii* infections.

In an aspect, the invention provides methods of treating an *A. baumannii* infection in a subject by providing to a subject infected with *A. baumannii* rifabutin and a second antibiotic. The second antibiotic may be a polymyxin (e. g. colistin, polymyxin B, polymyxin B nonapeptide) or cefiderocol.

The subject may be infected with strain of *A. baumannii* that is resistant to one or more antibiotics. The strain may be resistant to one or more of an aminocyclitol, aminoglycoside, beta-lactam, beta-lactamase inhibitor, carbapenem, cephalosporin, polymyxin, quinolone, rifamycin, sulfonamide, minocycline, eravacycline, sulbactam, and tetracycline. The strain may be resistant to one or more of amikacin, trimethoprim-sulfamethoxazole, cefepime, cefiderocol, ceftazidime, chloramphenicol, ciprofloxacin, colistin, polymyxin B, doripenem, gentamicin, imipenem, levofloxacin, meropenem, penicillin, piperacillin, rifabutin, rifampicin, tazobactam, and tigecycline.

Each antibiotic may be administered by a separate route of administration. Two or more of the antibiotics may be administered by the same route of administration. Each antibiotic may independently be administered intravenously, orally, parenterally, subcutaneously, by inhalation, by injection, and/or by infusion.

Each antibiotic may be administered in a separate formulation. Two or more of the antibiotics may be administered in a single formulation. The antibiotics may be administered according to the same dosing regimen, or two or more antibiotics may be administered according to different dosing regimens. The dosing regimen may include one or more of a dosage, dosage frequency, or interval between dosages.

The subject may be a human. The subject may be a pediatric, a newborn, a neonate, an infant, a child, an adolescent, a pre-teen, a teenager, an adult, or an elderly subject. The subject may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

The method may include providing one or more antibiotics in addition to the first two antibiotics, e.g., rifabutin and either colistin or cefiderocol. The one or more additional antibiotics may be an aminocyclitol, aminoglycoside, beta-lactam, beta-lactamase inhibitor, carbapenem, cephalosporin, polymyxin, quinolone, rifamycin, sulfonamides, minocycline, eravacycline, sulbactam, and tetracycline. The one or more additional antibiotics may be amikacin, trimethoprim-sulfamethoxazole, cefepime, cefiderocol, ceftazidime, chloramphenicol, ciprofloxacin, colistin, doripenem, gentamicin, imipenem, levofloxacin, meropenem, penicillin, piperacillin, polymyxin B, rifabutin, rifampicin, tazobactam, and tigecycline.

In another aspect, the invention provides combination therapies that include rifabutin and a second antibiotic in a therapeutically effective amount to treat an *A. baumannii* infection in a subject. The second antibiotic may be a polymyxin (e. g. colistin, polymyxin B, polymyxin B nonapeptide) or cefiderocol.

The subject may be infected with strain of *A. baumannii* that is resistant to one or more antibiotics, such as any of those described above.

Each antibiotic may be administered by a separate route of administration. Two or more of the antibiotics may be administered by the same route of administration. Each antibiotic may independently be administered intravenously, orally, parenterally, subcutaneously, by inhalation, by injection, and/or by infusion.

Each antibiotic may be administered in a separate formulation. Two or more of the antibiotics may be administered in a single formulation. The antibiotics may be administered according to the same dosing regimen, or two or more antibiotics may be administered according to different dosing regimens. The dosing regimen may include one or more of a dosage, dosage frequency, or interval between dosages.

The subject may be human or a class of humans, such as any of those described above.

The combination therapy may include providing, in a therapeutically effective amount, one or more additional antibiotics, such as any of those described above.

In another aspect, the invention provides uses of combinations the include rifabutin and a second antibiotic for making one or more medicaments for treating an *A. baumannii* infection in a subject. The second antibiotic may be colistin or cefiderocol.

In embodiments of the use, the subject may be infected with strain of *A. baumannii* that is resistant to one or more antibiotics, such as any of those described above.

In embodiments of the use, each antibiotic is administered by a separate route of administration. In embodiments of the use, two or more of the antibiotics are administered by the same route of administration. In embodiments of the use, each antibiotic is independently be administered intravenously, orally, parenterally, subcutaneously, by inhalation, by injection, and/or by infusion.

In embodiments of the use, each antibiotic is administered in a separate formulation. In embodiments of the use, two or more of the antibiotics are administered in a single formulation. In embodiments of the use, the antibiotics are administered according to the same dosing schedule. In embodiments of the use, two or more of the antibiotics are administered according to different dosing schedules. The dosing schedule may include one or more of a dosage, dosage frequency, or interval between dosages.

In embodiments of the use, the subject is a human or a member of a class of humans, such as any of those described above.

In embodiments of the use, the combination includes one or more additional antibiotics, such as any of those described above.

DETAILED DESCRIPTION

Figure 1:
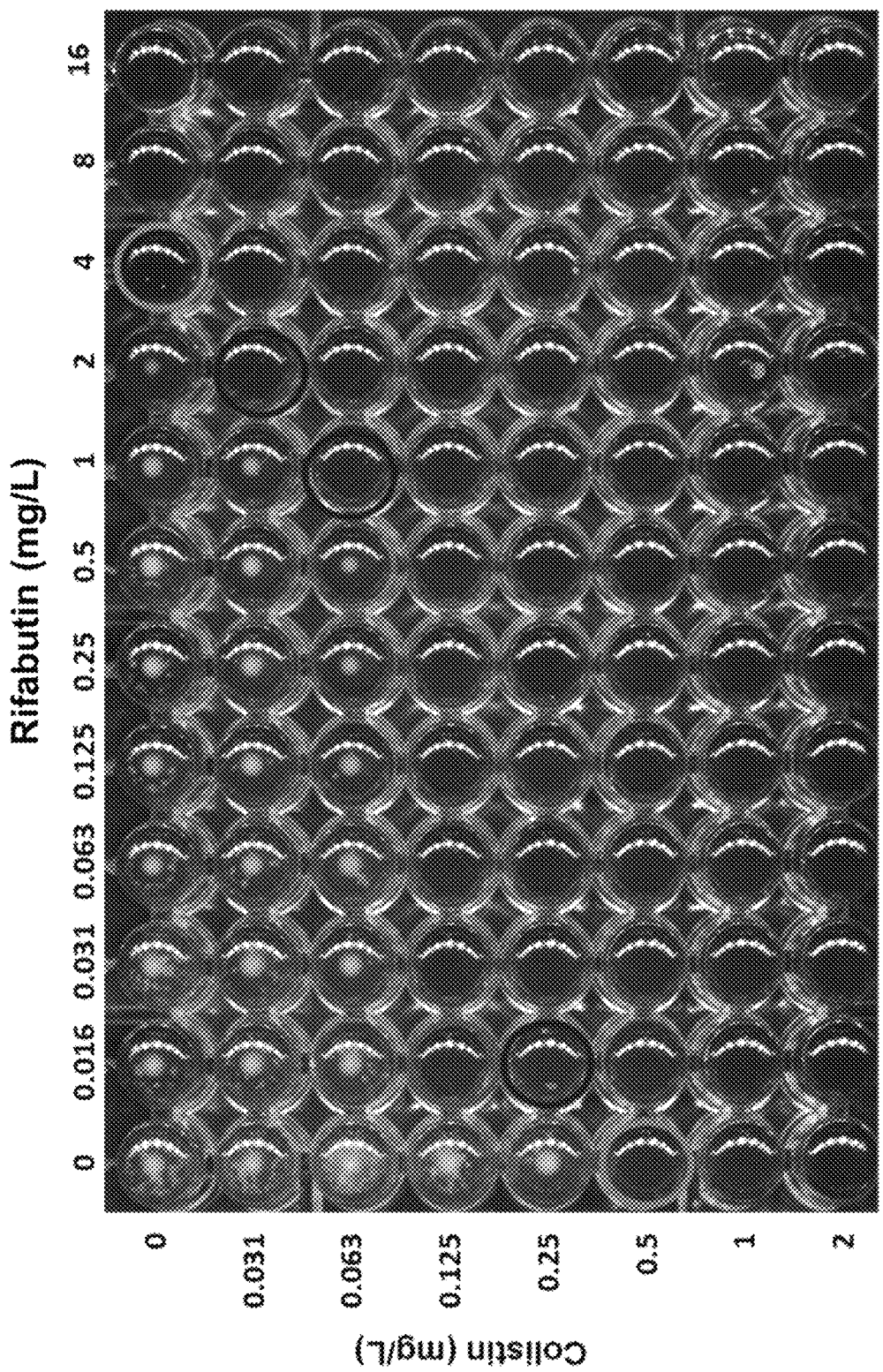
FIG. 1 is an image of a 96-well plate checkerboard of *A. baumannii* cells cultured in various concentrations of rifabutin and colistin.

The invention provides combination therapies for treating an *A. baumannii* infection in a subject. The combination therapies are based on the finding that rifabutin acts synergistically with antibiotics such as colistin and cefiderocol to inhibit growth of *A. baumannii* cells. Therefore, the use of rifabutin in combination with either colistin or cefiderocol is more effective than use of any of those antibiotics alone in treating *A. baumannii* infections. Moreover, and unexpectedly, the combination of rifabutin and colistin are even effective against *A. baumannii* strains that are resistant to both of the antibiotics when given individually but become susceptible to treatment when given in combination.

Combination Therapies

The combination therapies of the invention include two antibiotics that act synergistically to inhibit growth of *A. baumannii* cells. Synergy between antibiotics, such as a rifabutin and colistin, may be determined by any suitable method. One method includes determining the minimum inhibitory concentration (MIC) for each antibiotic individually and in combination and calculating a Fractional Inhibitory Concentration Index (FICI) as follows:

$$FICI = \left(\frac{MICA_{combination\ A+B}}{MIC_{antibiotic\ A}}\right) + \left(\frac{MICB_{combination\ A+B}}{MIC_{antibiotic\ B}}\right)$$

The pair of antibiotics is characterized as acting synergistically or not based on the FICI according to the following criteria: synergy (FICI ≤0.5); indifferent (FICI >0.50 and ≤4); antagonistic (FICI >4). Determining synergy of antibiotics based on the FICI is described in, for example, Jenkins, S. G. & Schuetz, A. N. Current Concepts in Laboratory Testing to Guide Antimicrobial Therapy. Mayo Clin. Proc. 87, 290-308 (2012), the contents of which are incorporated herein by reference.

The combination therapies of the invention, one of the antibiotics is rifabutin. The combination therapies include a second antibiotic that act synergistically with the rifabutin. The second antibiotic may be a polymyxin, such as colistin, or a cephalosporin, such as cefiderocol. Colistin may be provided as colistimethate sodium or colistin sulfate. The combination therapies may include additional antibiotics, e.g., they may include 3, 4, 5, or more different antibiotics. Each antibiotic may independently be an aminocyclitol, aminoglycoside, beta-lactam, beta-lactamase inhibitor, carbapenem, cephalosporin, polymyxin, quinolone, rifamycin, sulfonamide, minocycline, eravacycline, sulbactam, or tetracycline. Each antibiotic may independently be amikacin, trimethoprim-sulfamethoxazole, cefepime, cefiderocol, ceftazidime, chloramphenicol, ciprofloxacin, colistin, doripenem, gentamicin, imipenem, levofloxacin, meropenem, penicillin, piperacillin, polymyxin B, rifabutin, rifampicin, tazobactam, or tigecycline.

Rifabutin is a dark red-violet powder, has a molecular formula of $C_{46}H_{62}NO_{11}$, a molecular weight of 847.02 and the following structure:

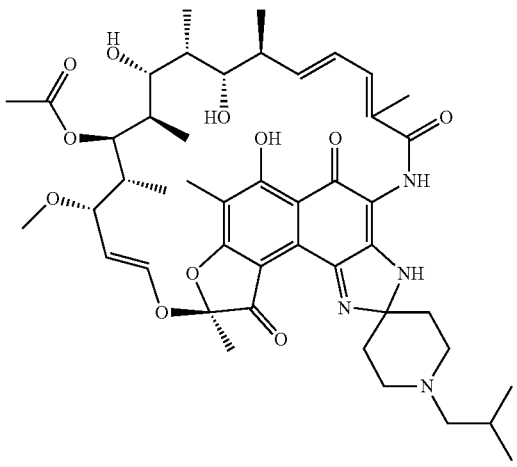 [SMILES: CO[C@H]1/C=C/O[C@@]2(C)Oc3c(C)c(O)c4c(c3C2=O)C2=NC3(CCN(CC(C)C)CC3)NC2=C(NC(=O)/C(C)=C/C=C/[C@H](C)[C@H](O)[C@@H](C)[C@@H](O)[C@@H](C)[C@H](OC(C)=O)[C@@H]1C)C4=O]

Rifabutin has a broad spectrum of antimicrobial activity. It is considerably more active than rifampin against MAC, *M. tuberculosis*, and *M. leprae*. It is also active against most atypical mycobacteria, including *M. kansasii; M. chelonae*, however, is relatively resistant. Rifabutin is also active against staphylococci, group A streptococci, *N. gonorrhoeae, N. meningitidis, H. injluenzae, H. ducreyi, C. jejuni, H. pylori, C. trachomatis, T. gondii* and *A. baumannii*.

Each antibiotic may be administered by any suitable route of administration. For example, and without limitation, each antibiotic may independently be administered intravenously, orally, parenterally, subcutaneously, by inhalation, by injection, and/or by infusion.

One or more antibiotics in the combination therapies may be administered to the same dosing regimen. One or more antibiotics may be administered according to different dosing regimens. A dosing regimen may include a dosage, a schedule or administration, or both. A dosage may be described by an absolute amount of drug (e.g. mg), or by a relative amount of the drug to the subject (e.g. mg/kg). A schedule of administration may be described by the interval between doses. For example and without limitation, the interval between doses may be about an hour, about 2 hours, about 3 hours, about 4 hours, about 6 hours, about 8 hours, about 12 hours, about 24 hours, about 36 hours, about 48 hours, about 3 days, about 4 days, about 5 days, about 6 days, about 7 days, or more.

Formulations

One or more of the antibiotics may be provided in a single formulation. One or more antibiotics may be provided in separate formulations. Each formulation may be prepared for delivery by a particular route of administration, such as intravenously, orally, parenterally, subcutaneously, by inhalation, by injection, and/or by infusion.

The antibiotics may be provided as pharmaceutically acceptable salts, such as nontoxic acid addition salts, which are salts of an amino group formed with inorganic acids such as but not limited to hydrochloric acid, hydrobromic acid, phosphoric acid, sulfuric acid and perchloric acid or with organic acids such as, but not limited to, acetic acid, maleic acid, tartaric acid, citric acid, succinic acid, methansulfonic acid, glucuronic acid, malic acid, gluconic acid, lactic acid, aspartic acid, or malonic acid.

The formulation may be administered by injection, infusion, implantation (intravenous, intramuscular, subcutaneous, or the like) or by inhalation in dosage forms, formulations, or via suitable delivery devices or implants containing conventional, non-toxic pharmaceutically acceptable carriers, solvents, diluents, and adjuvants. The formulation and preparation of such compositions are well known to those skilled in the art of pharmaceutical formulation.

Formulations for parenteral use may be provided in unit dosage forms (e.g., in single-dose ampoules and vials), in vials containing several doses and in which a suitable preservative may be added (see below), in prefilled syringes, or in prefilled IV bags. The pharmaceutical compositions described herein may be in the form suitable for sterile injection.

Formulations may include solutions containing rifabutin. Rifabutin solutions and methods of making rifabutin solutions are described in co-owned U.S. Application No. 62/902,019, the contents of which are incorporated herein by reference.

Depending upon the needs of the patient, and the clinical conditions, administration of the composition by IV administration may be favored over oral administration because it allows for rapid introduction of the antibiotic into systemic circulation, provides complete bioavailability, allows to better control the pharmacokinetic parameters that are driving the pharmacological efficacy, and avoids issues of stability in the gastrointestinal tract and absorption.

The typical dosage of rifabutin is that able to reach plasma or local levels in which rifabutin $C_{max}$ is >2 mg/L but <50 mg/L and AUC is 10 mg*h/L<200 mg*h/L.

Formulations may be formulated for parenteral administration, such as by injection or infusion. The injection or infusion may be subcutaneous or intravenous.

Treating *A. baumannii* Infections

The combination therapies of the invention are useful for treating an *A. baumannii* infection in a subject. The subject may be a human. The subject may be a pediatric, a newborn, a neonate, an infant, a child, an adolescent, a pre-teen, a teenager, an adult, or an elderly subject. The subject may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

The subject may have an *A. baumannii* infection that is resistant to an antibiotic. For example and without limitation, the *A. baumannii* infection may be resistant to one or more of an aminocyclitol, aminoglycoside, beta-lactam, beta-lactamase inhibitor, carbapenem, cephalosporin, polymyxin, quinolone, rifamycin, sulfonamide, tetracycline, amikacin, trimethoprim-sulfamethoxazole, cefepime, cefiderocol, ceftazidime, chloramphenicol, ciprofloxacin, colistin, doripenem, gentamicin, imipenem, levofloxacin, meropenem, penicillin, piperacillin, rifabutin, rifampicin, tazobactam, and tigecycline. The *A. baumannii* infection may be resistant to rifabutin, colistin, or both. The *A. baumannii* infection may be resistant to rifabutin, cefiderocol, or both.

The antibiotics in the combination therapy may be administered simultaneously or sequentially. Sequential administration or alternating administration may include providing each antibiotic exclusively for a period of time. Sequential administration may include a period of overlap in which the subject is provided both the IV formulation containing rifabutin and the formulation containing the other therapeutic. The periods of exclusivity and periods of overlap may independently be 1 hour, 2 hours, 3 hours, 4 hours, 5 hours, 6 hours, 1 day, 2 days, 3 days, 4 days, 5 days, 6 days, 1 week or 2 weeks.

EXAMPLES

Summary

The goal of this study was to identify standard of care (SoC) antibiotics that synergize with rifabutin against *Acinetobacter baumannii*. Synergy was evaluated by checkerboard minimum inhibitor concentration (MIC) on multiple *A. baumannii* clinical isolates. Rifabutin synergy was first identified with colistin and cefiderocol tested on the LAC-4 strain. When tested on a panel of strains, rifabutin/cefiderocol synergy was observed on 100% of the strains with a ≥4-fold decrease in MIC of cefiderocol. Rifabutin/colistin synergy was observed in 100% of the strains, the synergy was strong and independent of the initial resistance level towards rifabutin or colistin. The activity of rifabutin was superior to that of rifampicin when combined with colistin because the synergy with rifampicin was dependent of the initial resistance level towards rifampicin and the presence or absence of rpoB mutations as described in the literature. Unexpectedly, the rifabutin/colistin combination was active on strains resistant to rifabutin (including isolates with rpoB mutations) and/or to colistin, indicating that the combination overcomes both resistances.

In conclusion, rifabutin has the ability to improve antibacterial activity of cefiderocol and colistin against *A. baumannii* strains.

Antibacterial Agents

BV-015-3219-001-02 (rifabutin, (batch no. 17008MR89D)) was manufactured by Olon S.p.A. and 10 g/L stock solutions were prepared in DMSO. Stock solutions of rifampicin (Sigma R3501) and cefiderocol (Synnovator SYNNAAX397783) were prepared at 10 mg/mL in DMSO. Stock solutions of colistin sulfate (Sigma C4461), meropenem (Sigma M2578), cefotaxime (Acros 45495), tobramycin (Sigma T1783), eravacycline (MedChemExpress HY-16980A), minocycline (Sigma M9511) and SPR741 (Spero Therapeutics, FullReg P0271508-1) were prepared at 10 mg/mL in water. Finally, stock solutions of ciprofloxacin (Sigma 17850) were prepared at 10 mg/ml in 0.1 N NaOH. Stock solutions were stored at −20° C. until use.

Bacterial Strains

The *A. baumannii* clinical isolates used in this study are from the BioVersys strain collection. The strains were stored at −80° C. as 20% (v/v) glycerol stock cultures.

Antimicrobial Susceptibility and Synergy Testing

Synergy of rifabutin with SoC antibiotics was tested using broth microdilution checkerboard method. Checkerboards were performed according to the CLSI parameters used for microbroth dilution MIC5. CA-MHB, iron-depleted CA-MHB (ID-CA-MHB) or RPMI supplemented with 10% FCS medium were used as specified and ID-CA-MHB was prepared according to CLSI guidelines. Rifabutin was serially diluted along the abscissa and the combination antibiotic diluted along the ordinate. This setup allows the combination of rifabutin and another antibiotic in increasing concentrations to provide a final classification of the combination based on a Fractional Inhibitory Concentration (FIC) Index (FICI) as follows: synergy (FICI ≤0.5); indifferent (FICI >0.50 and ≤4); antagonistic (FICI >4). FICI is calculated as follows:

$$FICI = \left(\frac{MICA_{combination\ A+B}}{MIC_{antibiotic\ A}}\right) + \left(\frac{MICB_{combination\ A+B}}{MIC_{antibiotic\ B}}\right)$$

Consequently, synergy is defined when there is at least a 4-fold decrease in the MIC of the antibiotics tested in combination compared with the MIC of the antibiotics tested alone.

Example 1

Rifabutin Synergizes with Colistin and Cefiderocol Against the *A. baumannii* Strain LAC-4.

Rifabutin synergy with SoC antibiotics was tested with checkerboard assay on the *A. baumannii* LAC-4 strain. The checkerboards were performed in CA-MHB or ID-CA-MHB for cefiderocol. Results are shown in Table 1.

TABLE 1

| Second antibiotic | FICI | Interpretation |
| --- | --- | --- |
| Colistin | 0.254 | synergy |
| Meropenem | 1 | indifferent |
| Cefotaxime | 1.5 | indifferent |
| Ciprofloxacin | 1.5 | indifferent |
| Tobramycin | 1.5 | indifferent |
| Cefiderocol* | 0.5 | synergy |
| Eravacycline | 1 | indifferent |
| Minocycline | 1 | indifferent |

*Cefiderocol was tested in ID-CA-MHB

Out of the 8 SoC antibiotics tested, only colistin and cefiderocol showed synergy with rifabutin, while the 6 others were indifferent.

FIG. 1 is an image of a 96-well plate checkerboard of *A. baumannii* cells cultured in various concentrations of rifabutin and colistin. The wells used to determine the MICs of the antibiotics alone are circled in green, the wells of the combination MICs are circled in blue, and the well used to calculate the FICI is circled in red.

Figure 2:
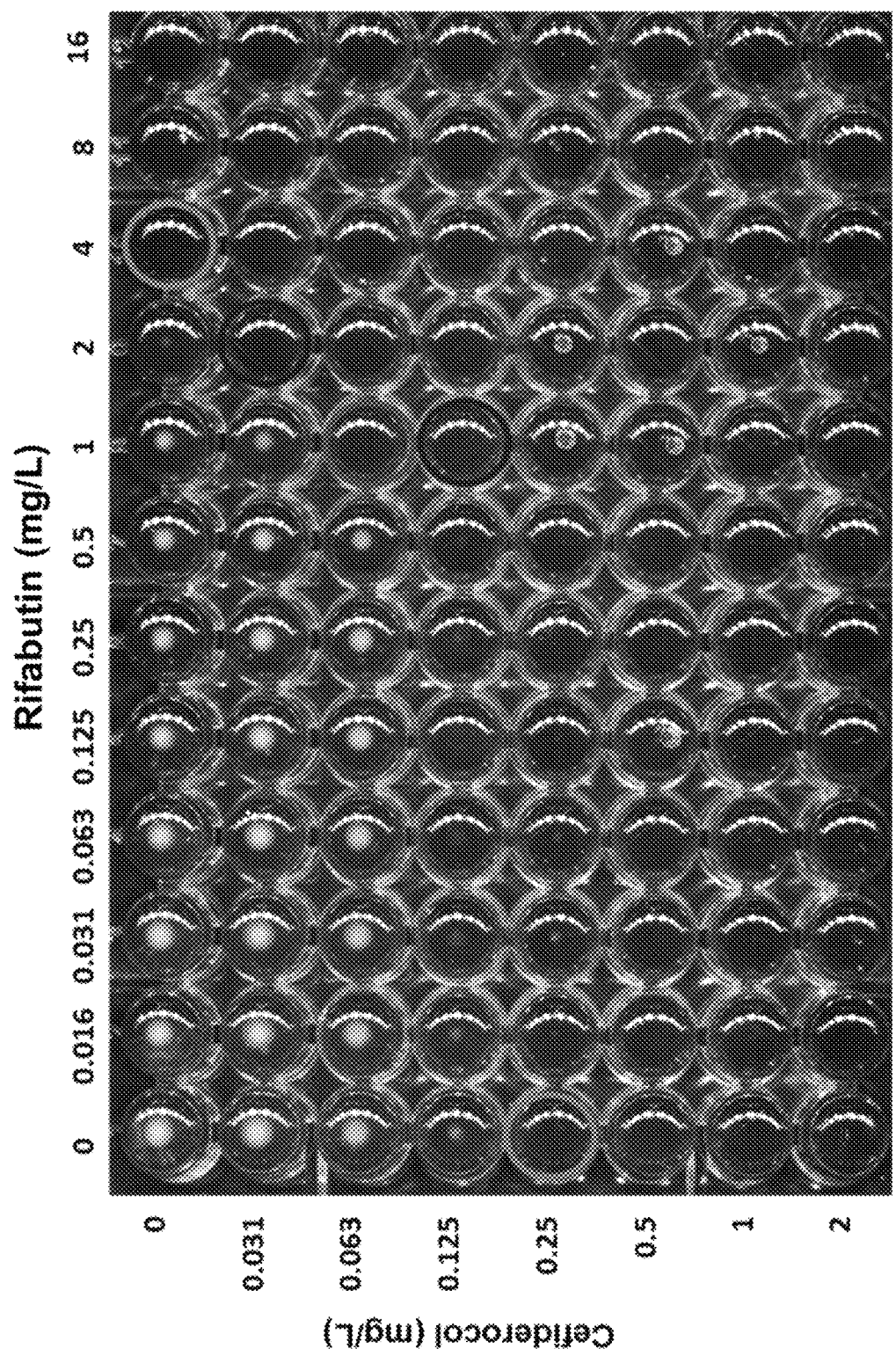
FIG. 2 is an image of a 96-well plate checkerboard of *A. baumannii* cells cultured in various concentrations of rifabutin and cefiderocol.

FIG. 2 is an image of a 96-well plate checkerboard of *A. baumannii* cells cultured in various concentrations of rifabutin and cefiderocol. The wells used to determine the MICs of the antibiotics alone are circled in green, the wells of the combination MICs are circled in blue, and the well used to calculate the FICI is circled in red.

Example 2

Rifabutin Decreases MICs of Cefiderocol of ≥4 Folds Against the *A. baumannii* Strains Tested.

To further study the synergy between rifabutin and cefiderocol against *A. baumannii*, checkerboards were performed on a panel of 16 MDR clinical isolates of *A. baumannii* including 5 isolates with elevated MICs 32 mg/L) to rifabutin (and rifampicin) having mutations in the rpoB gene. To describe in more detail the level of synergy, the MICs of rifabutin and cefiderocol, alone and in combination, together with the fold shift associated with these MICs are presented for each strain in Table 2. As expected, cefiderocol in combination with rifabutin had little or no effect on activity of rifabutin towards isolates with mutations in the rpoB gene. Unexpectedly, rifabutin produced at least a 4-fold decrease in the MIC of cefiderocol against all the *Acinetobacter baumannii* strains tested.

TABLE 2

| | Rifabutin MICs (mg/L) | | | Cefiderocol MICs (mg/L) | | |
|---|---|---|---|---|---|---|
| Strain | alone | combi | fold shift | alone | combi | fold shift |
| HUMC1 | 4 | 4 | 1 | 2 | 0.5 | 4 |
| UNT091-1 | 8 | 2 | 4 | 4 | 1 | 4 |
| IHMA690517 | 4 | 4 | 1 | 0.25 | 0.06 | 4 |
| IHMA863866 | 4 | 0.125 | 16 | 4 | 1 | 4 |
| IHMA919656 | 4 | 4 | 1 | 0.125 | 0.03 | 4 |
| IHMA1013816 | 4 | 4 | 1 | 0.06 | 0.016 | 4 |
| LAC-4** | 4 | 1 | 4 | 1 | 0.25 | 4 |
| UNT238-1** | 4 | 4 | 1 | 4 | 1 | 4 |
| UNT191-1** | 8 | 0.5 | 16 | 16 | 4 | 4 |
| UNT239-1** | 4 | 1 | 4 | 4 | 1 | 4 |
| UNT087-1 | 8 | 4 | 2 | 0.5 | 0.125 | 4 |
| 402292-17 | >128 | 128 | >1 | >32 | 8 | >4 |
| 402608-17 | 128 | 32 | 4 | 8 | 2 | 4 |
| IHMA867231 | >128 | 128 | >1 | 1 | 0.25 | 4 |
| 401046-18** | 32 | 16 | 2 | 128 | 32 | 4 |
| 401255-18 | 32 | 16 | 2 | 16 | 4 | 4 |

**Synergy determined in ID-CA-MHB.

Overall, the data indicate that combining rifabutin with cefiderocol may improve the treatment outcome of *A. baumannii* infections.

Example 3

Rifabutin Shows Strong Synergy with Colistin on 100% of the *A. baumannii* Strains Tested.

The same exercise was performed for rifabutin synergy with colistin towards *A. baumannii*. Checkerboards were performed on a panel of 16 MDR clinical isolates of *A. baumannii* including 5 isolates with elevated MICs 32 mg/L) to rifabutin (and rifampicin) having mutations in the rpoB gene and 5 colistin resistant strains (MIC ≥4 mg/L). Synergy was tested in CA-MHB medium which is the approved media to test colistin MIC. Results are shown in Table 3. Unexpectedly, colistin in combination with rifabutin had a pronounced effect on activity of rifabutin towards isolates with a mutation in the rpoB gene. In these cases the shift in rifabutin MIC was 32-fold in combination with colistin.

TABLE 3

| | Synergy in CA-MHB | | | | | |
|---|---|---|---|---|---|---|
| | rifabutin MICs (mg/L) | | | Colistin MICs (mg/L) | | |
| Strain | alone | combi | fold shift | alone | combi | fold shift |
| HUMC1 | 4 | 0.125 | 32 | 0.5 | 0.125 | 4 |
| UNT091-1 | 8 | <0.03 | >256 | 0.5 | 0.125 | 4 |
| IHMA690517 | 8 | 0.06 | 128 | 16 | 0.5 | 32 |
| IHMA863866 | 4 | 0.06 | 64 | >512 | 1 | >512 |
| IHMA919656 | 4 | 0.03 | 128 | 512 | 1 | 512 |
| IHMA1013816 | 8 | 0.125 | 64 | 16 | <0.5 | >32 |
| LAC-4 | 4 | 0.016 | 256 | 0.5 | 0.125 | 4 |
| UNT238-1 | 8 | 2 | 4 | 0.25 | 0.06 | 4 |
| UNT191-1 | 16 | <0.03 | >512 | 2 | 0.5 | 4 |
| UNT239-1 | 4 | 1 | 4 | 1 | 0.25 | 4 |
| UNT087-1 | 16 | 0.5 | 32 | 1 | 0.25 | 4 |
| 402292-17 | >128 | 4 | 32 | 1 | 0.25 | 4 |
| 402608-17 | 128 | 2 | 64 | 1 | 0.25 | 4 |
| 401255-18 | 128 | 2 | 64 | 0.25 | 0.06 | 4 |
| IHMA867231 | >128 | 2 | >64 | 32 | 4 | 8 |
| 401046-18 | 64 | 1 | 64 | 0.5 | 0.125 | 4 |

Rifabutin synergy with colistin was observed in 100% of the strains when tested in CA-MHB. Strikingly, synergy was independent of the rifabutin or colistin original resistance levels as exemplified in CA-MHB where the colistin MICs are reduced by at least 16-fold in the colistin resistant strains turning all but one of them colistin sensitive. These results indicate that combining rifabutin with colistin has the potential to overcome both rifabutin and colistin resistance in *A. baumannii* clinical isolates.

These observations could indicate colistin having a role of a cell permeabilizer to synergize with rifabutin. To assess if colistin is only playing the role of a permeabilizer agent, rifabutin synergy was tested in combination with the colistin derivative SPR741 that retains permeabilization activity but loses antibacterial activity. Results are shown in Table 4.

TABLE 4

| | Rifabutin/SPR741 synergy | | | |
|---|---|---|---|---|
| | Rifabutin MICs (mg/L) | | | SPR741 MICs in |
| Strain | alone | combi | fold shift | combination (mg/L) |
| HUMC1 | 4 | 0.25 | 16 | 4 |
| UNT091-1 | 0.25 | 0.06 | 4 | 2 |
| IHMA690517 | 4 | 1 | 4 | 16 |
| IHMA863866 | 4 | 2 | 2 | 16 |
| IHMA919656 | 8 | 1 | 8 | 8 |
| IHMA1013816 | 8 | 2 | 4 | 16 |
| ACC00535 | 8 | 0.5 | 16 | 4 |
| LAC-4 | 4 | 0.06 | 64 | 4 |
| UNT238-1 | 4 | 0.125 | 32 | 4 |
| UNT191-1 | 8 | 0.5 | 16 | 4 |
| UNT239-1 | 4 | 0.25 | 16 | 4 |
| UNT087-1 | 8 | 0.25 | 32 | 8 |
| 402292-17 | >32 | 2 | >16 | 32 |
| 402608-17 | >32 | 2 | >16 | 16 |
| IHMA867231 | >32 | >32 | 1 | 32 |
| 401046-18 | >32 | 2 | >16 | 8 |
| 401255-18 | >32 | 2 | >16 | 4 |

Rifabutin synergy with SPR741 was observed in 88% of the strains. However, the synergy was less pronounced compared to colistin synergy with, for most of the strains, rifabutin combination MICs remaining in the range of 0.125-2 mg/L. Moreover, the SPR741 concentration required to achieve synergy with rifabutin was at least 8-fold higher than the one of colistin. The results indicate that the intrinsic antibacterial activity of colistin is required for strong synergy with rifabutin.

Example 4

Comparison of Rifampicin Synergy in Combination with Colistin Against *A. baumannii* Isolates.

As a comparator, rifampicin synergy with colistin was determined on the panel of *A. baumannii* strains. Results are shown in Table 5.

TABLE 5

| | Rifampicin/colistin synergy | | | | | |
|---|---|---|---|---|---|---|
| | Rifampicin MICs (mg/L) | | | Colistin MICs (mg/L) | | |
| Strain | alone | combi | fold shift | alone | combi | fold shift |
| HUMC1 | 4 | 1 | 4 | 0.5 | 0.125 | 4 |
| UNT091-1 | 4 | 0.125 | 32 | 0.5 | 0.125 | 4 |
| IHMA690517 | 4 | 0.06 | 64 | 16 | <0.5 | >32 |
| IHMA863866 | 2 | 0.125 | 16 | 512 | 0.5 | 1024 |
| IHMA919656 | 2 | 0.03 | 64 | 512 | 1 | 512 |
| IHMA1013816 | 2 | 0.06 | 32 | 32 | <0.5 | >64 |

TABLE 5-continued

| | Rifampicin/colistin synergy | | | | | |
| --- | --- | --- | --- | --- | --- | --- |
| | Rifampicin MICs (mg/L) | | | Colistin MICs (mg/L) | | |
| Strain | alone | combi | fold shift | alone | combi | fold shift |
| LAC-4 | 2 | 0.06 | 32 | 0.5 | 0.125 | 4 |
| UNT238-1 | 2 | 0.125 | 16 | 0.5 | 0.125 | 4 |
| UNT191-1 | 4 | 0.25 | 16 | 1 | 0.25 | 4 |
| UNT239-1 | 2 | 0.25 | 8 | 1 | 0.25 | 4 |
| UNT087-1 | 4 | 4 | 1 | 0.5 | 0.125 | 4 |
| 402292-17 | 512 | 256 | 2 | 0.25 | 0.125 | 4 |
| 402608-17 | 512 | 64 | 8 | 1 | 0.25 | 4 |
| IHMA867231 | 512 | 32 | 16 | 32 | 4 | 8 |
| 401046-18 | 512 | 64 | 8 | 0.25 | 0.06 | 4 |
| 401255-18 | 512 | 128 | 4 | 0.25 | 0.06 | 4 |

Synergy was observed on 88% of the strains. As for rifabutin, synergy was independent of the colistin resistance level as illustrated by the synergy on most of the colistin resistant strains. However, in contrast to rifabutin, and expected from literature, rifampicin/colistin synergy was weak on isolates with mutations in the rpoB gene. For these isolates the rifampicin combination MICs remaining high ($\geq 32$ mg/L).

Overall, it was demonstrated showed that colistin can improve rifabutin activity, and vice versa, against *A. baumannii* strains that have elevated MICs toward rifabutin, colistin, or both. However, unlike rifampicin there was an unexpected activity of rifabutin in combination with colistin towards isolates which have mutations in the rpoB gene which would otherwise be resistant to the antibiotics.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A method of treating an *A. baumannii* infection in a subject, the method comprising providing to a subject infected with *A. baumannii* rifabutin and a second antibiotic selected from the group consisting of colistin and cefiderocol.

2. The method of claim 1, wherein the subject is infected with a strain of *A. baumannii* that is resistant to rifabutin.

3. The method of claim 1, wherein the subject is infected with a strain of *A. baumannii* that is resistant to the second antibiotic.

4. The method of claim 1, wherein the second antibiotic is colistin.

5. The method of claim 1, wherein the second antibiotic is cefiderocol.

6. The method of claim 1, wherein the rifabutin is administered intravenously.

7. The method of claim 1, wherein the rifabutin is administered by inhalation.

8. The method of claim 1, wherein the rifabutin and the second antibiotic are provided in a single formulation.

9. The method of claim 1, wherein the rifabutin and the second antibiotic are provided separately.

10. The method of claim 1, wherein the *A. baumannii* comprises a rpoB mutation.

11. A combination therapy comprising rifabutin and a second antibiotic selected from the group consisting of colistin and cefiderocol, wherein the combination therapy comprises rifabutin and the second antibiotic in a therapeutically effective amount to treat an *A. baumannii* infection in a subject.

12. The combination therapy of claim 11, wherein the subject is infected with a strain of *A. baumannii* that is resistant to rifabutin.

13. The combination therapy of claim 11, wherein the subject is infected with a strain of *A. baumannii* that is resistant to the second antibiotic.

14. The combination therapy of claim 11, wherein the second antibiotic is colistin.

15. The combination therapy of claim 11, wherein the second antibiotic is cefiderocol.

16. The combination therapy of claim 11, wherein the rifabutin is administered intravenously.

17. The combination therapy of claim 11, wherein the rifabutin is administered by inhalation.

18. The combination therapy of claim 11, wherein the rifabutin and the second antibiotic are provided in a single formulation.

19. The combination therapy of claim 11, wherein the rifabutin and the second antibiotic are provided separately.

20. The combination therapy of claim 11, wherein the *A. baumannii* comprises a rpoB mutation.

* * * * *